(12) United States Patent  
Jensen et al.

(10) Patent No.: US 11,324,444 B2  
(45) Date of Patent: May 10, 2022

(54) EEG MONITOR

(71) Applicant: T&W Engineering A/S, Lynge (DK)

(72) Inventors: Rasmus Stig Jensen, Birkerod (DK); Richard Topholm, Holte (DK); Erik Skov Christensen, Hillerod (DK); Rasmus Elsborg Madsen, Charlottenlund (DK)

(73) Assignee: T&W Engineering A/S, Lynge (DK)

( * ) Notice: Subject to any disclaimer, the term of this patent is extended or adjusted under 35 U.S.C. 154(b) by 638 days.

(21) Appl. No.: 15/557,327

(22) PCT Filed: Mar. 18, 2015

(86) PCT No.: PCT/EP2015/055646  
§ 371 (c)(1),  
(2) Date: Sep. 11, 2017

(87) PCT Pub. No.: WO2016/146183  
PCT Pub. Date: Sep. 22, 2016

(65) Prior Publication Data  
US 2018/0049692 A1 Feb. 22, 2018

(51) Int. Cl.  
*A61B 5/00* (2006.01)  
*A61B 5/145* (2006.01)  
*A61B 5/291* (2021.01)  
*A61B 5/369* (2021.01)

(52) U.S. Cl.  
CPC ........ *A61B 5/4839* (2013.01); *A61B 5/14532* (2013.01); *A61B 5/291* (2021.01); *A61B 5/369* (2021.01); *A61B 5/6815* (2013.01); *A61B 5/6817* (2013.01); *A61B 5/7264* (2013.01); *A61B 5/746* (2013.01); *A61B 5/4205* (2013.01)

(58) Field of Classification Search  
None  
See application file for complete search history.

(56) References Cited

U.S. PATENT DOCUMENTS

| 6,572,542 B1 * | 6/2003 | Houben | A61B 5/0472 |
| | | | 600/300 |
| 2006/0064037 A1 * | 3/2006 | Shalon | A61B 5/0006 |
| | | | 600/586 |
| 2007/0060830 A1 | 3/2007 | Le et al. | |

(Continued)

FOREIGN PATENT DOCUMENTS

| JP | 2013517856 A | 5/2013 |
| WO | 2011091856 A1 | 8/2011 |
| WO | 2014010165 A1 | 1/2014 |

OTHER PUBLICATIONS

Communication dated Sep. 18, 2018 from Japanese Patent Office in counterpart application No. 2017-566191.

(Continued)

*Primary Examiner* — Matthew Kremer  
*Assistant Examiner* — Samuel C Kim  
(74) *Attorney, Agent, or Firm* — Sughrue Mion, PLLC

(57) ABSTRACT

An EEG monitor (1) including electrodes (17) adapted for capturing EEG signals and a signal processing part (11) which is adapted for analyzing and classifying the EEG signals captured. The signal processing part (11) is adapted for identifying electrical signals captured by the electrodes (17) that are derived from muscular activity related to the process of chewing.

15 Claims, 4 Drawing Sheets

(56) References Cited

U.S. PATENT DOCUMENTS

| | | | |
|---|---|---|---|
| 2009/0007918 A1 | 1/2009 | Darkin et al. | |
| 2009/0287107 A1 | 11/2009 | Beck-Nielsen et al. | |
| 2010/0317955 A1 | 12/2010 | Madsen et al. | |
| 2011/0071464 A1* | 3/2011 | Palerm | A61B 5/14532 604/66 |
| 2012/0302858 A1* | 11/2012 | Kidmose | A61B 5/0476 600/379 |
| 2013/0274580 A1* | 10/2013 | Madsen | A61B 5/04018 600/365 |
| 2014/0118138 A1* | 5/2014 | Cobelli | A61B 5/4848 340/539.12 |
| 2014/0347265 A1* | 11/2014 | Aimone | A61M 21/00 345/156 |
| 2015/0352282 A1* | 12/2015 | Mazlish | G16Z 99/00 604/504 |
| 2016/0012749 A1* | 1/2016 | Connor | G09B 5/00 600/13 |

OTHER PUBLICATIONS

Search Report and Written Opinion dated Jul. 17, 2018 from Singapore intellectual Property Office in counterpart application No. 11201707661Q.
International Search Report for PCT/EP2015/055646 dated Jan. 18, 2016.

* cited by examiner

EEG MONITOR

CROSS REFERENCE TO RELATED APPLICATIONS

This application is a National Stage of International Application No. PCT/EP2015/055646 filed Mar. 18, 2015, the contents of which are incorporated herein by reference in their entirety.

BACKGROUND OF THE INVENTION

The present invention relates to an EEG monitor. The present invention more specifically relates to an EEG monitor having electrodes adapted for capturing an EEG signal and further comprising a signal processing part adapted for analyzing and classifying signals captured by EEG electrodes. The invention further relates to a system for adjusting the blood glucose level of a person.

EEG is the commonly used abbreviation for Electro Encephalography, which is generally speaking a method of electrically monitoring brain activity of a person. Systems for monitoring EEG have been known for many years. However with the general technological development, EEG monitoring systems that may be carried or worn continuously by a person to be monitored have been devised.

One goal is to have personal wearable EEG monitors which are small enough to be carried without causing more inconvenience than glasses or a modern hearing aid.

Such EEG monitors may be applied for surveillance of persons having diabetes, where the brains reaction to low blood glucose is monitored in order to warn against hypoglycaemic attacks caused by low blood sugar levels. Hypoglycaemic events may lead to unconsciousness and even death. A system for such surveillance of an imminent hypoglycaemic attack is disclosed in WO-A-2006/066577.

An EEG monitor may be an implanted subcutaneous system or it may be a device arranged externally with electrodes on the skin surface or in the ear canal.

Combinations with an implanted electrode part and an external processor part, connected through an inductive link, have also been described in WO-A-2006/066577.

EEG monitors may also be applied in connection with insulin pumps to prevent that more insulin than needed is administered to the person.

Any information on issues which can affect the blood glucose level of a person can be relevant for the algorithm in an EEG monitor deciding to provide an alarm about a possible upcoming event of hypoglycaemia. Any such information will also be relevant for a system comprising an insulin pump and maybe a continuous glucose monitor (CGM).

One problem is that any such further input will either be dependent on input from an external source or from the person wearing the EEG monitor, both introducing a degree of uncertainty, or the input will depend on the presence of some sensor.

SUMMARY OF THE INVENTION

One solution of such a problem is an EEG monitor where the signal processing part is adapted for identifying electrical signals captured by the EEG electrodes that are derived from muscular activity related to the process of chewing.

One advantage of the solution is that chewing, and thereby possibly eating, is relevant information in relation to different relevant applications of continuous EEG monitoring, such as detecting an upcoming event of hypoglycaemia. Also in general EEG monitoring for research purposes, automatic registration of the time when a person is eating may be relevant.

In an embodiment of the EEG monitor the signal processing part is adapted for identifying an upcoming onset of hypoglycemia and for providing an alarm when such an upcoming onset of hypoglycemia is identified. A monitor which can detect chewing as well as an upcoming onset of hypoglycemia will be very relevant to use for people with diabetes. The alarm or notification of the EEG monitor may also depend on whether chewing is identified or not, i.e. the alarm or notification could be different when chewing is detected, since the person wearing the alarm may already be in the process of reducing the risk of hypoglycemia.

In a further embodiment the EEG monitor is adapted for arrangement in the ear region of a person to be monitored. The EEG monitor comprises an EEG sensing part having EEG electrodes. The EEG sensing part can be arranged subcutaneously at the scalp or in the ear canal. With this arrangement it is possible to detect a reliable EEG signal and to arrange the EEG monitor relatively discrete.

In a further embodiment the EEG monitor signal processing part comprises feature extraction and classifying parts both adapted for the detection of an electrical signal related to the process of chewing. This has been found to provide a reliable identification of chewing based on the frequencies and amplitudes present in a chewing signal.

In a further embodiment at least one of the feature extraction and classifying parts are adapted to be calibrated to detect a chewing signal for a specific person who are supposed to use said EEG monitor. This will make detection of chewing more reliable.

In a further embodiment the EEG monitor is adapted for recording acoustic sound and for applying such recording as a further parameter in classification of a signal as derived from chewing. Since the sound of chewing is a characteristic sound for most persons, the recording of sound by the EEG monitor may be applied in the signal processing for an even more reliable identification of chewing. The sound recording could be a further input to the feature extraction.

In a second aspect, the invention is related to a system for adjusting the blood glucose level of a person. This system comprises an EEG monitor as mentioned above, and an insulin delivery device configured to release insulin into the body of said person. Detection of chewing is highly relevant for such a system administering insulin to diabetics.

In an embodiment of this system the EEG monitor is adapted for submitting a message to said insulin delivery device or insulin pump when chewing is identified. Depending on the diabetes of the person, the insulin pump can be pre-programmed to apply this information in different ways.

In a further embodiment of the system, the EEG monitor is adapted for identifying an upcoming onset of hypoglycemia and is configured to submit a warning signal to the insulin delivery device or insulin pump, if an upcoming onset of hypoglycemia is identified. This warning message causes the insulin delivery device or insulin pump to restrict the insulin delivery for a predetermined time period. This has the purpose of avoiding hypoglycemia. Furthermore, the restriction of the insulin delivery can be made dependent on whether chewing is identified or not, such that the decrement in insulin administration is relatively smaller when chewing is identified compared to when chewing is not identified. This has the purpose of avoiding an unnecessary high increase of the blood glucose level since the person wearing the system is likely to already being taking action to increase the blood glucose level.

BRIEF DESCRIPTION OF THE DRAWINGS

Embodiments of the invention will now be explained in further detail with reference to the figures.

DETAILED DESCRIPTION OF THE INVENTION

Figure 1:
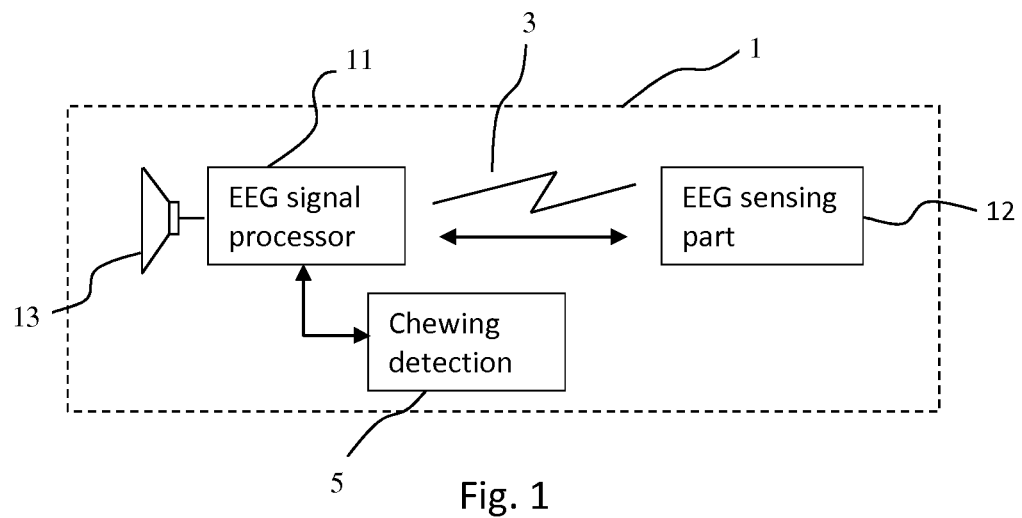
FIG. 1 illustrates an EEG monitor.

FIG. 1 illustrates an EEG monitor 1 which is adapted to be arranged in the ear region of the person who is to be monitored. The EEG monitor 1 comprises two main parts: An EEG sensing part 12 and an EEG signal processor part 11. Further to this the EEG monitor also comprises a component, e.g. a speaker 13, for providing alarms or messages. The EEG monitor 1 will also comprise a power supply, e.g. in the form of a battery.

The EEG sensing part 12 has electrodes for detecting an EEG signal. The EEG sensing part 12 comprises EEG electrodes which may be arranged subcutaneous at the scalp, preferably in a region extending from behind the ear and towards the top of the scalp. The EEG electrodes may also be arranged as surface skin electrodes in the ear canal. The EEG electrodes may be of the type having direct electric connection to the tissue or the skin, or they may be of the capacitive type, where a dielectric material is arranged between the electric conductive part of the electrode and the tissue or skin. The advantages of having the EEG electrodes either subcutaneous or in the ear canal are that good and clear EEG signals can be received, and that the electrodes in these positions will be more protected from picking up electromagnetic noise from the surroundings compared to a position external on the scalp.

The connection 3 between the EEG sensing part 12 and the EEG signal processor part 11 is either wireless, when the EEG sensing part is implanted, or wired, when the EEG sensing part is arranged in the ear canal.

The subcutaneous or ear canal positions of the EEG electrodes are preferred also from a cosmetic perspective. The subcutaneous or ear canal positions are furthermore preferred from a reliability point of view since these positions facilitate durable and stable contact to either tissue or skin, i.e. the risk of losing contact, and thereby not being able to detect an EEG signal, is significantly smaller compared to an external electrode which is more likely to lose contact, e.g. during exercise or other daily activities.

The EEG signal processor part 11 is adapted to receive the EEG signal from the EEG sensor and to process the signal in order to extract specific features from the measured EEG signal. This feature extraction can be related to e.g. specific frequencies and amplitudes in the EEG signal. Such extracted features may be classified in order to determine if they are relevant to identify an upcoming onset of hypoglycemia. In this context information of other sources than the EEG signal will be relevant. One such information is if the person wearing the EEG monitor is eating, and that an increase in blood glucose level therefore is to be expected.

The EEG monitor comprises or is connected to a chewing detection unit 5 which is part of, or connected to, the EEG signal processor. The chewing detection unit 5 may comprise a feature extractor, for extracting features from the EEG signal, as well as a classifier, for classifying the features in order to make a qualified decision on whether the person wearing the EEG monitor is chewing or not.

Since chewing is a strong indicator that a person may be eating, detection of muscle activity related to eating can be an important input to an algorithm deciding when to provide an alarm to the person carrying the EEG monitor. If chewing is detected this may be a reason to delay an alarm in order to see if an upcoming onset of hypoglycemia is avoided by the food being eaten. However, this is an important decision were care should be taken to be on the safe side when setting up or programming the EEG monitor, i.e. personal characteristics of how fast the person carrying the monitor actually develops hypoglycemia should be taken into account when deciding if an alarm can be delayed when chewing is detected, or if a different type of alarm or message should be provided instead.

The EEG signal processor is preferably connected to a speaker in order to provide an alarm of an upcoming onset of hypoglycemia to the user of the system.

If the EEG monitor is applied as part of a system for control of the blood glucose level in a person having diabetes, e.g. a system comprising an insulin pump and maybe a CGM, information on chewing and possibly eating may be highly relevant when deciding on bolus doses. E.g. if the person is supposed to request bolus doses before eating, and chewing for an extended period of time is detected without the person has requested a bolus dose, a notification could be provided to the person.

Figure 2:
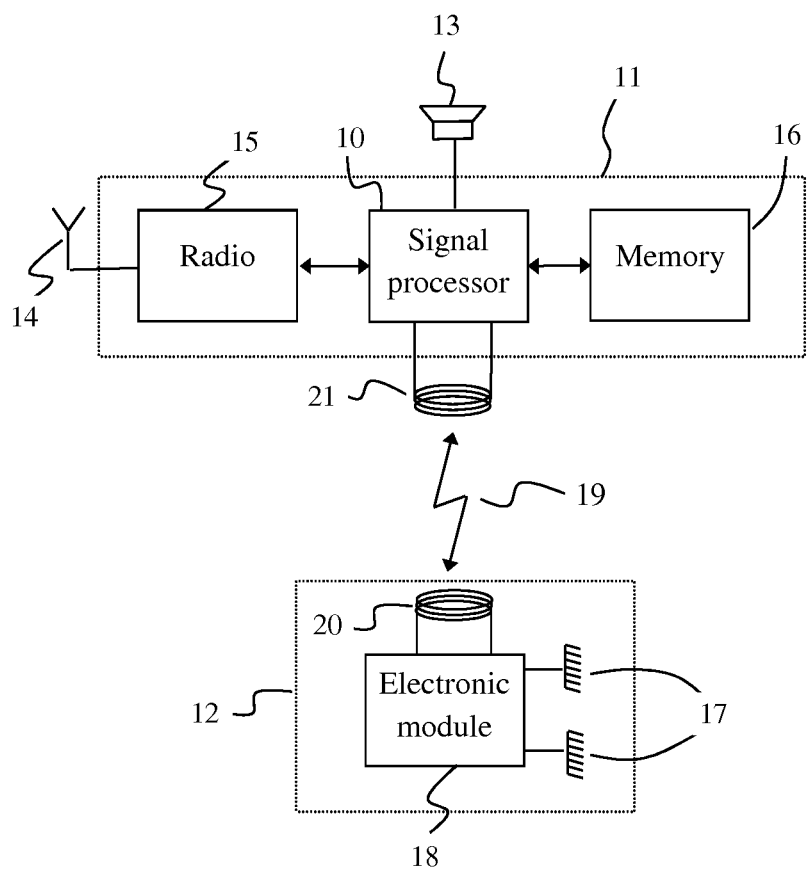
FIG. 2 illustrates an EEG monitor having an EEG sensing part and an EEG signal processor part.

FIG. 2 shows an example of the EEG monitor in more details. The EEG monitor 1 comprises an external EEG signal processor part 11 and an implantable EEG sensing part 12. The EEG sensing part 12, suitable for being subcutaneously positioned behind the ear of a person, comprises subcutaneous EEG electrodes 17 connected to an electronic module 18. The number of EEG electrodes is at least two. Often at least three electrodes or even at least four electrodes are preferred. The electronic module 18, which is shown in more detail in FIG. 4, often comprises an A/D converter 24, a communications controller 26, and a voltage regulator 27. The electrodes 17 are connected to the A/D converter; the communications controller is connected to a first coil 20 of an inductive link 19.

The EEG signal processor part 11 comprises a signal processor 10 having a controller (not shown) connected to a second coil 21 of the inductive link 19. The signal processor 10 is further connected to a battery (not shown) for power supply and to a loudspeaker 13 for providing an acoustic signal, e.g. an alarm, in the event that an upcoming onset of hypoglycemia is identified. The EEG signal processor part 11 also comprises a memory 16, e.g. for logging of data, as well as a radio 15 with an antenna 14 for wireless communication with external units (not shown), which might be applied as a remote control, for storage of data, for forwarding alarms to other persons or for uploading data or information, e.g. to an Internet server. Communication may also be with other components of a system for controlling the blood glucose level of a person. E.g. communication can be with an insulin pump or a CGM unit.

When in use, the EEG signal processor part 11 may be placed behind the ear of a person for whom monitoring of an EEG signal is desired, and in the vicinity of a subcutaneously implantable EEG sensing part 12, which preferably is implanted right below the skin and slightly behind the ear of the user and positioned in such a way that a reliable, electrical EEG signal may be detected by the electrodes 17.

Figure 3:
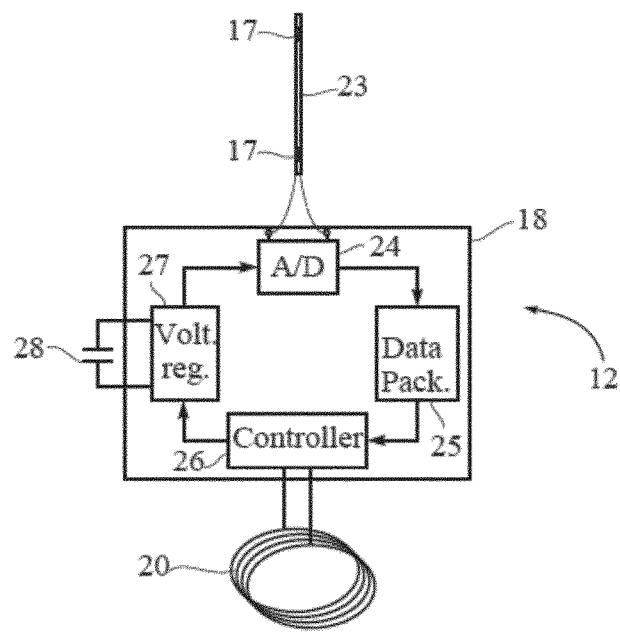
FIG. 3 illustrates an example of an EEG sensing part.

As illustrated in more details in FIG. 3 the electrodes 17 of the EEG sensing part 12 can be arranged in one cable 23 integrating the electrodes 17 arranged with contact to the tissue in limited areas along the length.

The electrodes 17 pick up EEG signals as a varying electrical voltage potential and feed the varying electrical voltage to the A/D converter 24 in the electronic module 18. The A/D converter 24 converts the varying electrical voltage into a digital signal and presents this digital signal to a data packet controller 25 which is part of the electronic module 18. The data packet controller 25 converts the digital signal into a stream of data packets according to a predetermined communications protocol, and feeds the resulting stream of data packets to the communications controller 26.

The communications controller 26 is configured to energize the electronic module 18 electromagnetically by receiving energy from the second coil 21 of the external EEG signal processor part 11 by the first coil 20. The electromagnetic energy received in the first coil 20 is transferred to the voltage regulator 27 which, together with a ceramic capacitor 28, is applied as a power source for the electronic module 18.

Furthermore, the communications controller 26 takes data packets representing the EEG signals from the electrodes 17 and transfers this digitized EEG signal from the EEG sensing part through the inductive link by modulating the load on the power received in the first coil 20 from the second coil 21. This modulated load is detectable from the EEG signal processor part 11, where the modulation of the load is converted into an electrical signal suitable for being continuously decoded and analyzed by the signal processor 10.

The analysis of the EEG signal in order to identify an upcoming onset of hypoglycemia may be based on different algorithms. One example on how this analysis can be performed is given in WO-A1-2012/069549.

Depending on the results of the analysis of the EEG signals, decisions may be taken by the signal processor 10 to activate the loudspeaker 13 sounding an alarm if an upcoming onset of hypoglycemia is identified. Such a decision may also be influenced by information that the person wearing the EEG monitor is chewing and eating, or the type of alarm or notification provided may be dependent on such information.

The EEG electrodes 17 in the embodiment shown in FIG. 3 are arranged to be implanted subcutaneously behind the ear of a user in order to provide a signal suitable for detection by the electronic module of the EEG sensing part 12. Often the wire 23 with the electrodes 17 is arranged to extend towards the top of the scalp, while the electronic module 12, also comprising the coil 20, will be arranged in the ear region at the site of implantation, e.g. right behind or right above the ear.

A typical output signal from the EEG electrode has a magnitude in the range of approximately 1 µV to 100 µV. Typically, the voltage signal detected by a subcutaneous electrode is larger than the signal at a skin or ear canal electrode. Muscular contractions usually generate voltage levels of a magnitude of 10 mV, but such signals are filtered out by the system. The intrinsic noise level of the electrode is about 1 µV RMS measured over a bandwidth from 0.1 to 100 Hz, and the useable bandwidth of the output signal is 0.1 to 40 Hz.

The EEG sensing part 12 is encased in a bio-compatible material (not shown), such as a ceramic. The electrodes are also made from a bio-compatible metal, such as a platinum-iridium alloy. When the EEG signal processor part 11 is worn behind the ear (as a behind-the-ear hearing aid) where the implant has been positioned, the second coil 21 of the EEG signal processor part 11 will be a few millimeters from the first coil 20 of the EEG sensing part 12. This facilitates communication and transfer of power between the EEG signal processor part 11 and the EEG sensing part 12. The two coils should preferably be closely aligned, whereby a more efficient transfer of power and a more reliable communication can be achieved.

The EEG sensing part of the EEG monitor is described as implantable in relation to FIGS. 2 and 3. However, the EEG sensing part can also be arranged in the ear canal with the electrodes detecting the EEG signal from the skin surface of the ear canal. An example of an ear plug with electrodes for this purpose is given in WO-A1-2011/000383.

Figure 4:
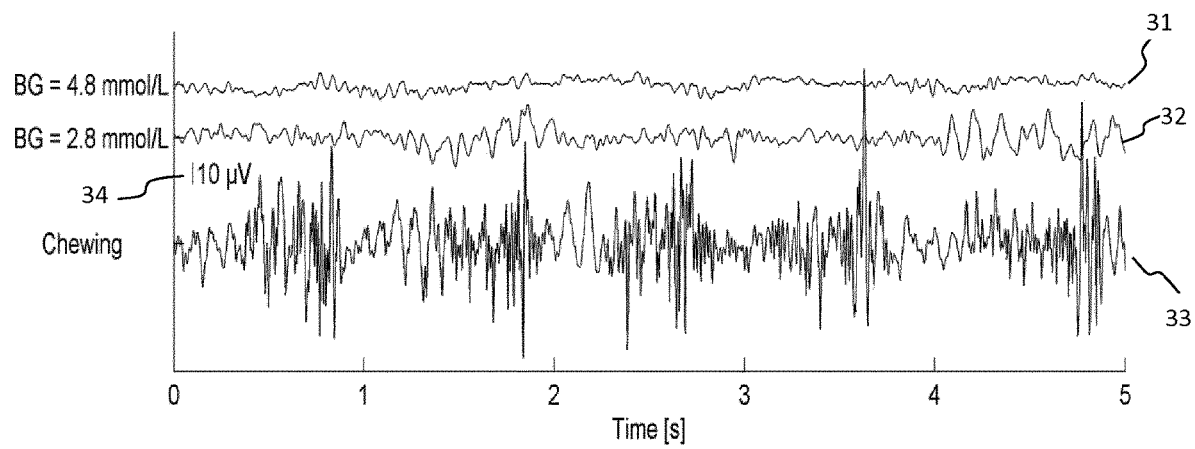
FIG. 4 illustrates a graph with a signal from chewing compared to an EEG signal.

FIG. 4 shows a graph with examples of EEG signals 31, 32 captured by an EEG monitor, and with an electrical signal derived from chewing and captured by the same EEG monitor. The top signal 31 is a normal EEG signal where the person's blood glucose level is 4.8 mmol/liter. The second signal 32 is an EEG signal detected when the person's blood glucose level is 2.8 mmol/liter. This signal indicates that onset of hypoglycemia may be upcoming. The third signal 33 has been caused by chewing. It is clear that the amplitudes of this signal are significantly larger. The size range of the signal amplitudes are indicated by the short vertical line 34, the length of which is equivalent to a magnitude of 10 microvolt.

A calibration for the person to use an EEG monitor may be preferred in order for the monitor to be able to identify a chewing signal from this person. Such a calibration may be performed as a type of machine learning where the person is chewing on food, maybe even on different types of food. The signal recorded by the EEG electrodes is analyzed and especially features which are not also present in the EEG signal when the person is not chewing on food are identified. Such features can then be used for later detection of chewing. Such features may be based on frequency, amplitude, energy content, entropy, specific time constants etc.

The features should be selected such that electrical signals from other muscular activity, or from eye movement, yawning or talking are not taken as a chewing signal.

The advantage here is that the muscles applied for chewing are situated closer to the behind-the-ear positions and the above-the-ear positions than any other muscles.

Figure 5:
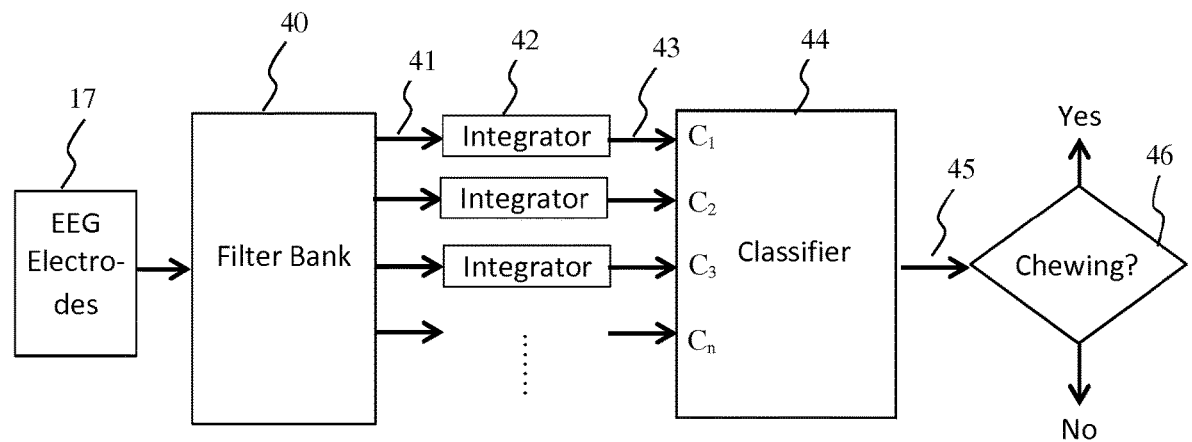
FIG. 5 illustrates an example of feature extraction and classification for identification of chewing.

FIG. 5 shows an example of a system for identification of chewing. Here, the principle of extraction of features of the signal from the EEG electrodes, and the following classification is illustrated schematically. The EEG electrode signal is directed to a filter bank 40, usually after some amplification (not shown). The filter bank will divide the signal into a number of frequency band signals 41, each comprising the part of the EEG electrode signal present in the specific frequency range. Each frequency band signal is integrated in an integrator 42 for a given time period. The integrator could be a first order filter. The output of the several integrators 42 may be referred to as features 43. These features 43 could be obtained also by an FFT (Fast Fourier Transform) analysis of the signal from the electrodes 17.

The features 43, or the output of the integrators, are directed to a classifier 44, which applies a predetermined coefficient $C_1 \ldots C_n$ to each of the n features. So, the example in FIG. 5 applies a linear classifier. The classifier calculates a decision value 45 which is submitted to a decision block 46 determining whether there is chewing or not in the original signal.

The coefficients $C_1 \ldots C_n$ of the classifier 44 should be selected carefully. For this purpose machine learning is applied with a number of samples of signals, where some of the samples include chewing and some do not. These samples of signals are each marked as either including chewing or not. The features 43 of these samples are provided to a Support Vector Machine (SVM) as a training set. The SVM can then set up the optimum coefficients for the linear classifier. Some of the samples should also comprise signals from sources which are likely to be present in practice, e.g. by the person blinking with the eyes or talking. The EEG monitor must be able to identify chewing with a high degree of certainty, also when such other signals are present.

The classifier may have to be adjusted in this way individually to each person who is to apply the EEG monitor, in order to obtain the most reliable decision on whether the person is chewing or not. This individual set-up may be necessary because the exact placement of EEG electrodes may vary between persons, and because the electrical signals (EEG, muscular activity related to chewing and other muscular activity) will also vary between persons.

It may be necessary to instruct persons who will use an EEG monitor that is also detecting the presence of a chewing signal, that the use of chewing gums should be avoided. However, the signal from chewing food may be different from the signal from chewing on chewing gum. In order for the EEG monitor to detect this difference, a more detailed calibration related to the person will be performed, and a careful testing of such a calibration executed, as required.

The discerning of a chewing signal from other muscle activities is helped both by a placement of the EEG electrodes in the ear region or on the head, e.g. subcutaneously, where no other major muscles than the jaw muscles are close, and also by the more characteristic rhythm of chewing. Thereby, the difference in signal strength and in rhythm may facilitate a more reliable identification of the presence of a chewing signal.

Figure 6:
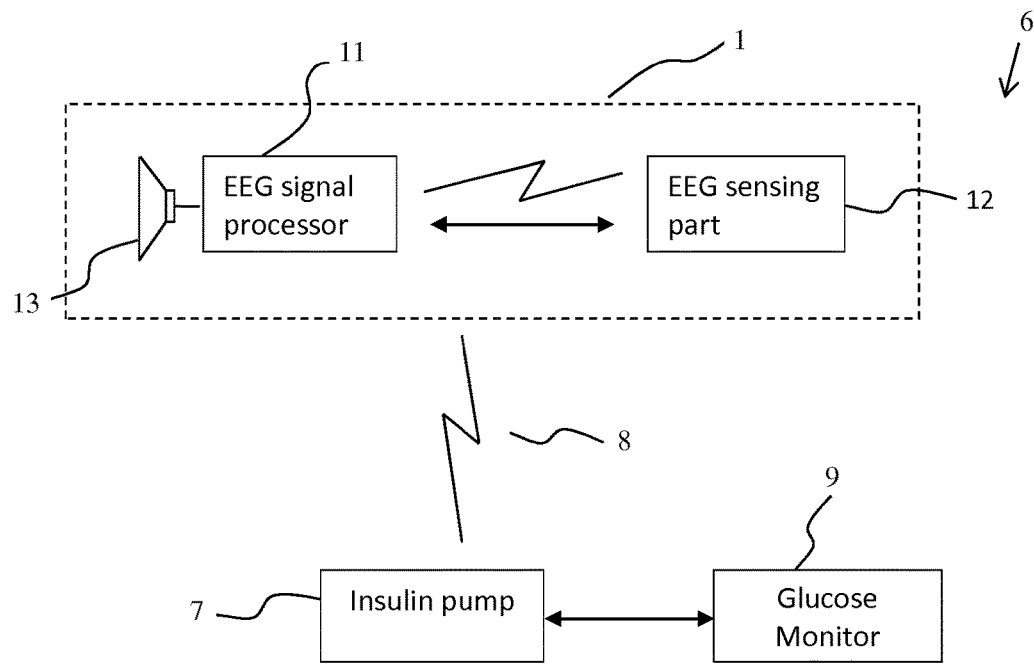
FIG. 6 illustrates a system with an EEG monitor, an insulin pump and a glucose monitor.

FIG. 6 illustrates an example of a system 6 with an EEG monitor 1, an insulin delivery device or an insulin pump 7 and maybe also a glucose monitor 9, which could be a CGM. The EEG monitor 1 and the insulin pump 7 are connected by a wireless connection 8. The glucose monitor 9 has the possibility for entering a measured glucose level into the insulin pump 7. The insulin pump will administer insulin to the person wearing the system 6. The administered dose of insulin will partly be determined from a preset program with adjustments dependent on inputs from the glucose monitor, from the person wearing the system and from the EEG monitor. Such a system will allow for a more precise adjustment of the insulin delivery aiming at holding the blood glucose level within an optimum interval. Especially the further information provided by the EEG monitor, including the detection of chewing, will make such a system more reliable. The information on chewing may be used for deciding the type of alarm or notification provided to the person.

Figure 7:
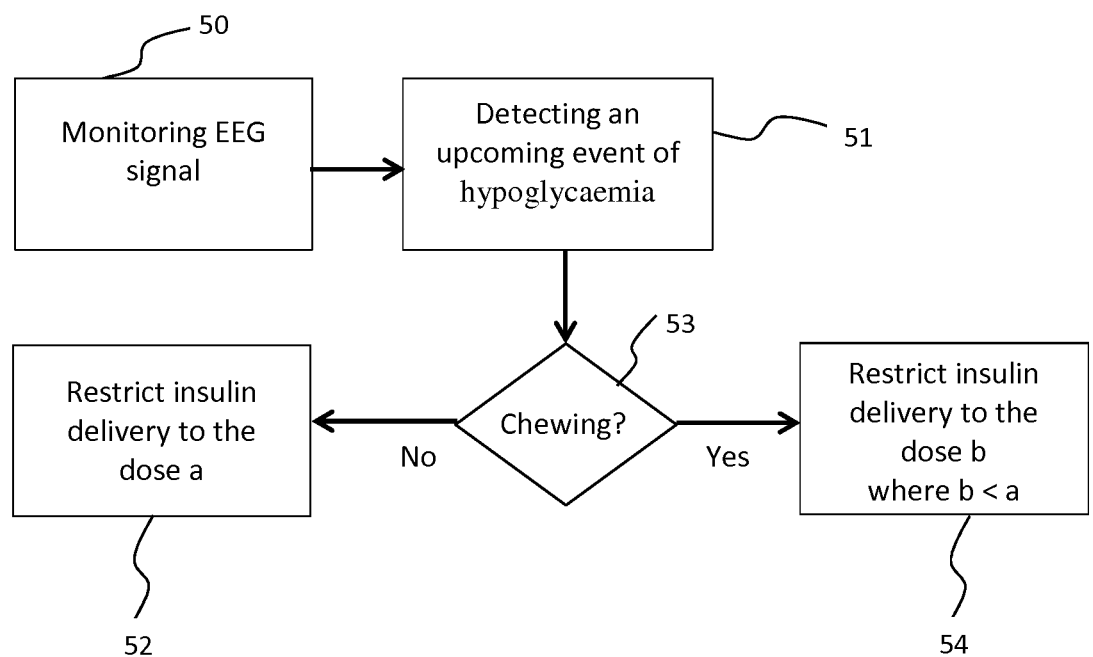
FIG. 7 illustrates a flowchart of a method applying chewing information in a system with an EEG monitor as in FIG. 6.

FIG. 7 illustrates an example of one way of applying the feasibility of chewing detection in the EEG monitor 1 in the system 6 of FIG. 6. In the case that an upcoming onset of hypoglycemia is identified, it will be controlled immediately if the person wearing the system is chewing and maybe also if the person has been chewing for a predetermined period of time. The latter is dependent on logging of the chewing information, e.g. in a circular buffer holding this information for some time, e.g. 10 minutes or longer. I.e. the EEG monitor would always know if the person using the EEG monitor is chewing, and maybe also what fraction of the time within the last e.g. 5 or 10 minutes have been spent on chewing.

So, when the continuous EEG monitoring 50 results in the detection 51 of an upcoming event of hypoglycemia, the further action is dependent on a decision 53 on whether chewing is detected or not, and maybe also on the amount of chewing within a short time period.

One possibility is, that if chewing is not detected the insulin pump will restrict the insulin delivery to the dose a (box 52), which is a smaller dose than the dose which would otherwise have been provided. On the other hand, if chewing is detected, and chewing has been going on for at least a predetermined fraction of the time within the last e.g. 5 minutes, the insulin dose is restricted to the dose b (box 54), which is also a smaller dose than the dose which would otherwise have been provided, but where the dose b is larger than the dose a. All doses that the insulin pump can provide should be pre-selected under the supervision of a physician with good knowledge of the diabetes of the person to use the system.

Obviously, the administered insulin dose will also depend on any measured glucose level, and an alarm or at least a notification will may also be provided to the person.

The invention claimed is:

1. An EEG monitor comprising EEG electrodes adapted for capturing EEG signals and a signal processing part adapted for analyzing and classifying the EEG signals captured to detect a hypoglycemia-related condition, and for causing further action to be taken in response to said hypoglycemia-related condition, wherein said signal processing part is adapted for identifying electrical signals captured by said electrodes that are derived from chewing-related muscular activity, and in response to detection of said hypoglycemia-related condition, said signal processing part is configured to take into account identification of the chewing-related muscular activity from the identified electrical signals in determining a type of said further action to be taken.

2. The EEG monitor according to claim 1, wherein said signal processing part is adapted for identifying an upcoming onset of hypoglycemia and for providing an alarm when said upcoming onset of hypoglycemia has been identified.

3. The EEG monitor according to claim 2, wherein said alarm is of a type dependent on whether chewing has been identified or not.

4. The EEG monitor according to claim 1, wherein the EEG monitor is adapted for being arranged in an ear region of a person to be monitored and comprises an EEG sensing part having the EEG electrodes, said EEG sensing part being configured to be arranged subcutaneously at a scalp or in an ear canal.

5. The EEG monitor according to claim 1, wherein said signal processing part comprises feature extraction and classifying parts both adapted for the identification of the electrical signals that are derived from the chewing-related muscular activity.

6. The EEG monitor according to claim 5, wherein at least one of said feature extraction and classifying parts are adapted to be calibrated to detect the chewing-related muscular activity for a specific person.

7. The EEG monitor according to claim 1, wherein said EEG monitor is further adapted for recording acoustic sound and for applying such recording as a further parameter in the identification of the electrical signals as derived from said chewing-related muscular activity.

8. A system for adjusting a blood glucose level of a person, comprising the EEG monitor according to claim 1, and further comprising an insulin delivery device configured to release insulin into the body of said person.

9. The system according to claim 8, wherein said EEG monitor is adapted for submitting a message to said insulin delivery device when chewing has been identified.

10. The system according to claim 9, wherein said EEG monitor is adapted for identifying an upcoming onset of hypoglycemia and is configured to submit a warning signal to said insulin delivery device if the upcoming onset of hypoglycemia has been identified, said warning signal causing said insulin delivery device to restrict the insulin delivery for a predetermined time period.

11. The system according to claim 10, wherein said restriction is made dependent on whether the chewing has been identified or not, wherein the insulin delivery device is configured such that the restriction in the insulin delivery is smaller when the chewing is identified compared to when the chewing is not identified.

12. The EEG monitor according to claim 1, wherein said hypoglycemia-related condition comprises an upcoming onset of hypoglycemia.

13. The EEG monitor according to claim 1, wherein said further action to be taken comprises a first action when said hypoglycemia-related condition is detected and said chewing-related muscular activity has not been identified, and a second action when said hypoglycemia-related condition is detected and said chewing-related muscular activity has been identified.

14. The EEG monitor according to claim 13, wherein said first action and said second action are two different alarm notifications.

15. The EEG monitor according to claim 13, wherein said first action is providing a notification of said hypoglycemia-related condition and said second action is providing said notification with a time delay.

* * * * *